United States Patent
Anwar (10) Patent No.: US 8,603,132 B2
(45) Date of Patent: Dec. 10, 2013

(54) SYSTEM AND METHOD FOR PROVIDING EMBOLIC PROTECTION

(75) Inventor: Azam Anwar, Dallas, TX (US)

(73) Assignee: Azam Anwar, Dallas, TX (US)

( * ) Notice: Subject to any disclaimer, the term of this patent is extended or adjusted under 35 U.S.C. 154(b) by 0 days.

(21) Appl. No.: 13/556,145

(22) Filed: Jul. 23, 2012

(65) Prior Publication Data
US 2012/0289918 A1 Nov. 15, 2012

Related U.S. Application Data

(62) Division of application No. 11/034,906, filed on Jan. 13, 2005, now Pat. No. 8,252,016.

(51) Int. Cl.
*A61M 29/00* (2006.01)

(52) U.S. Cl.
USPC .......................................................... 606/200

(58) Field of Classification Search
USPC .......................................................... 606/200
See application file for complete search history.

(56) References Cited

U.S. PATENT DOCUMENTS

| | | | |
|---|---|---|---|
| 4,676,782 A | 6/1987 | Yamamoto et al. | |
| 5,716,981 A | 2/1998 | Hunter et al. | |
| 5,800,525 A | 9/1998 | Bachinski et al. | |
| 5,882,329 A | 3/1999 | Patterson et al. | |
| 5,902,263 A | 5/1999 | Patterson et al. | |
| 5,910,154 A * | 6/1999 | Tsugita et al. | 606/200 |
| 6,051,014 A | 4/2000 | Jang | |
| 6,139,517 A | 10/2000 | Macoviak et al. | |
| 6,142,987 A | 11/2000 | Tsugita | |
| 6,168,579 B1 | 1/2001 | Tsugita | |
| 6,183,508 B1 | 2/2001 | Stinson et al. | |
| 6,210,363 B1 | 4/2001 | Esch et al. | |
| 6,287,321 B1 | 9/2001 | Jang | |
| 6,336,934 B1 * | 1/2002 | Gilson et al. | 606/200 |
| 6,398,756 B2 | 6/2002 | Peterson et al. | |
| 6,416,490 B1 | 7/2002 | Ellis et al. | |
| 6,450,989 B2 | 9/2002 | Dubrul et al. | |
| 6,485,502 B2 | 11/2002 | Michael et al. | |
| 6,508,783 B2 | 1/2003 | DeVore | |
| 6,530,914 B1 | 3/2003 | Mickley | |
| 6,547,759 B1 | 4/2003 | Fisher | |
| 6,582,400 B1 | 6/2003 | Hawk et al. | |
| 6,589,232 B1 | 7/2003 | Mueller | |
| 6,589,264 B1 | 7/2003 | Barbut et al. | |
| 6,592,546 B1 | 7/2003 | Barbut et al. | |
| 6,595,958 B1 | 7/2003 | Mickley | |
| 6,602,241 B2 | 8/2003 | Makower et al. | |
| 6,613,017 B1 | 9/2003 | Mickley | |
| 6,616,626 B2 | 9/2003 | Crank et al. | |
| 6,616,682 B2 * | 9/2003 | Joergensen et al. | 606/200 |
| 7,163,549 B2 | 1/2007 | Crank et al. | |
| 2001/0016726 A1 | 8/2001 | Dubrul et al. | |
| 2001/0027307 A1 | 10/2001 | Dubrul et al. | |
| 2001/0031982 A1 | 10/2001 | Peterson et al. | |
| 2001/0049517 A1 | 12/2001 | Zadno-Azizi et al. | |
| 2001/0053921 A1 | 12/2001 | Jang | |
| 2002/0016564 A1 | 2/2002 | Courtney et al. | |

(Continued)

*Primary Examiner* — Melanie Tyson
(74) *Attorney, Agent, or Firm* — Patent Capital Group (57) ABSTRACT

An apparatus for offering embolic protection is provided that includes a sponge operable to be positioned in an area of a patient who is to undergo a cardiovascular procedure. The sponge is operable to collect debris present in or proximate to the area and to allow a portion of blood flow or no blood flow associated with the area to continue while the debris is collected.

11 Claims, 6 Drawing Sheets

(56) References Cited

U.S. PATENT DOCUMENTS

| | | |
|---|---|---|
| 2002/0026145 A1 | 2/2002 | Bagaoisan et al. |
| 2002/0049486 A1 | 4/2002 | Knudson et al. |
| 2002/0072673 A1 | 6/2002 | Yamamoto et al. |
| 2002/0072699 A1 | 6/2002 | Knudson et al. |
| 2002/0161392 A1 | 10/2002 | Dubrul |
| 2002/0169436 A1 | 11/2002 | Gurm et al. |
| 2002/0188276 A1 | 12/2002 | Evans et al. |
| 2003/0023227 A1 | 1/2003 | Zadno-Azizi et al. |
| 2003/0028379 A1 | 2/2003 | Wendt et al. |
| 2003/0051735 A1 | 3/2003 | Pavcnik et al. |
| 2003/0065345 A1 | 4/2003 | Weadock |
| 2003/0065356 A1 | 4/2003 | Tsugita et al. |
| 2003/0153806 A1 | 8/2003 | Miller |
| 2003/0163081 A1 | 8/2003 | Constantz et al. |
| 2003/0171771 A1 | 9/2003 | Anderson et al. |
| 2003/0187475 A1 | 10/2003 | Tsugita et al. |

* cited by examiner

SYSTEM AND METHOD FOR PROVIDING EMBOLIC PROTECTION

CROSS-REFERENCE TO RELATED APPLICATION

This Application is a divisional of (and claims the benefit of priority under 35 U.S.C. §120 and §121) U.S. application Ser. No. 11/034,906, filed Jan. 13, 2005 now U.S. Pat. No. 8,252,016, entitled "System and Method for Providing Embolic Protection", naming Azam Anwar as inventor. The disclosure of the prior Application is considered part of and is incorporated by reference in the disclosure of this Application.

TECHNICAL FIELD OF THE INVENTION

This invention relates in general to cardiovascular diseases and, more particularly, to a process, a system, and a method for providing embolic protection in a cardiovascular environment.

BACKGROUND OF THE INVENTION

The treatment of cardiovascular diseases has grown exponentially in terms of sophistication and diversity. Procedures involving items such as stents and balloons are virtually routine in most heart-care practices. One problem associated with any cardiovascular procedure is debris and/or clots, which can be detrimental to a patient's health. Debris is generally a byproduct of plaque, which is a friable material. Hence, during a routine stent, bypass, or balloon procedure, debris can be present. During any such procedure, the debris may dislodge, fragment, or flake off and propagate to undesired areas of the patient. Such debris can manifest itself in the form of new blockages or blood clots: both of which can easily lead to heart attacks, strokes, kidney failures, amputations, etc.

Thus, these issues can be problematic for the patient and for the treating physician. Moreover, this harmful brittle material must be accounted for because it is so delicate, friable, and easily disturbed. Therefore, the ability to properly account for debris during a given cardiovascular procedure presents a significant challenge for physicians relegated the difficult task of controlling this issue.

SUMMARY OF THE INVENTION

From the foregoing, it may be appreciated by those skilled in the art that a need has arisen for an improved process for achieving superior embolic protection during any number of cardiovascular procedures and processes. In accordance with an embodiment of the present invention, a process, a system, and a method for controlling debris and embolus are provided that substantially eliminate or greatly reduce disadvantages and problems associated with conventional cardiovascular disease approaches, strategies, and instruments.

According to an embodiment of the present invention, an apparatus for offering embolic protection is provided that includes a sponge operable to be positioned in an area of a patient who is to undergo a cardiovascular procedure. The sponge is operable to collect debris present in or proximate to the area and to allow a portion of or no blood flow associated with the area to continue while the debris is collected.

In more particular embodiments, the apparatus may include a guide wire (of any suitable length) coupled to the sponge. Additionally, the apparatus may include one or more additional sponges that are coupled to the guide wire and that are operable to facilitate the portion of the blood flow while collecting the debris. In more specific embodiments, the sponge that is used during the cardiovascular procedure is operable to perform a sweeping function in the area when it is removed.

Alternatively, the sponge includes one or more edges that limit snagging in the area when the sponge is moved. In still other alternative embodiments, the sponge includes one or more grooves that are operable to collect the debris and to deposit at least a portion of the debris in a reservoir included in the sponge.

Certain embodiments of the present invention may provide a number of technical advantages. For example, according to one embodiment of the present invention, an architecture and a process are provided that offer a flexible system, which can easily conform to the shape of the target location. This would allow the present invention to have a broad range of applications, and be used in any number of (potentially awkward) environments. Moreover, the proffered sponge system of the present invention is atraumatic, as it offers only a minimal disruption to an associated surgical (or intervened) region.

In addition, the configuration of the sponge system is "always on," providing a solution that is continuously deployed and that consistently protects any vulnerable region within a given patient. Thus, the sponge system of the present invention is always actuated, which provides a number of additional benefits. For example, because of the "always on" feature, a surgeon is no longer burdened with having to trigger any type of filtering mechanism during a procedure. Also, the sponge is completely actuated once it emerges from a delivery catheter. This actuation exists during a procedure, during preparation for the procedure, and during the post-procedure tasks (e.g. removing instruments). The sponge system only stops being effective once it has been removed from the patent site. Moreover, the sponge system allows for perfusion, as blood flow is not unnecessarily restricted. This would allocate more procedure time for a physician to complete his objectives.

The present invention also provides for enhanced versatility in its applications, as it can readily be applied to virtually any procedure. This could include operations and protocols that involve the carotid artery, as well as numerous other vascular procedures.

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIGS. 5A-N are simplified schematic diagrams of various example configurations of the sponge system according to some of the teachings of the present invention.

DETAILED DESCRIPTION OF THE INVENTION

For purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

During cardiovascular procedures, there is a need to catch debris going downstream (i.e. any area in the downstream direction of blood flow). This need is particularly important in arteries, or in vein grafts. Note that a number of procedures (e.g. stents, balloons, etc.) involve friable materials that have a propensity to break apart and generate unwanted debris. The field is generally referred to as "embolic protection." The term "debris" as used herein in this document refers to any undesired or unwanted material at (or proximate to) the surgery site/area. This debris could be present anywhere in the vasculature and/or in any number of cardiovascular procedures (e.g. involving an aorta, graft, balloon angioplasty, carotid artery, renal artery, femoral artery, lower leg location, etc.).

The term "collect" as used herein in this document refers to any activity associated with capturing, confining, attracting, holding, or catching debris in a given area. The term "sponge" as used herein in this document refers to any compressible material, which may or may not be sponge-like in its structure, for collecting debris. The sponge may be designed based on any particular compression properties and, accordingly, be fitted or manufactured with particular cardiovascular environments in mind. Considerable flexibility is provided by the sponge of the present invention, as it can be modified, changed, or configured in any suitable structure or arrangement.

Current devices to address embolic protection are diverse in their protocols, strategies, and technologies. For example, some tools employ the use of a balloon. During such a balloon endeavor, a given conduit or passageway can be occluded, whereby subsequent work is performed, and prevalent debris is prohibited from moving downstream. Other devices include the use of a wire-based mesh device, which reflects a basket-type apparatus. Whether it is a proximal occlusion or a rudimentary filtering net, these devices and approaches suffer from a number of shortcomings.

For example, many of these devices are cumbersome, which requires even greater dexterity and precision for those individuals relegated the arduous task of performing associated cardiovascular operations. From an economic perspective, many of these devices are also problematic because they are expensive. Their excessive (and sometimes cost-prohibitive) price tags are generally due to their sophistication, complexity, and delicacy. Note that such heightened complexity in some of these devices demands a certain level of expertise to successfully operate them. Moreover, such delicate instruments are difficult to deliver, challenging to extract, and, further, are often inefficient in collecting debris.

At a more fundamental level, these devices are flawed because they simply fail to trap all of the debris at the target location. In some cases, this may be due to an imperfect occlusion. In other cases, these deficiencies in capturing material are present because the filtering system is faulty. From a flexibility standpoint, current systems are also unsatisfactory. Many configurations are simply too rigid and inflexible for their intended applications. Consider the case where an oblong canal is implicated by a given procedure. It is exceptionally difficult to protect such an awkward channel from potential debris that is present at the surgery site or area. In worst-case scenarios, a physician may opt to refrain from performing operations in such an area because the risk for debris may be too high. If the device is shaped in a crude manner such that friction is generated during contact with interior walls, then the device may cause undesired trauma and rupture the aforementioned plaque, as outlined supra. Note that many devices are constructed of metal, which is conducive to the identified trauma scenario.

Figure 1:
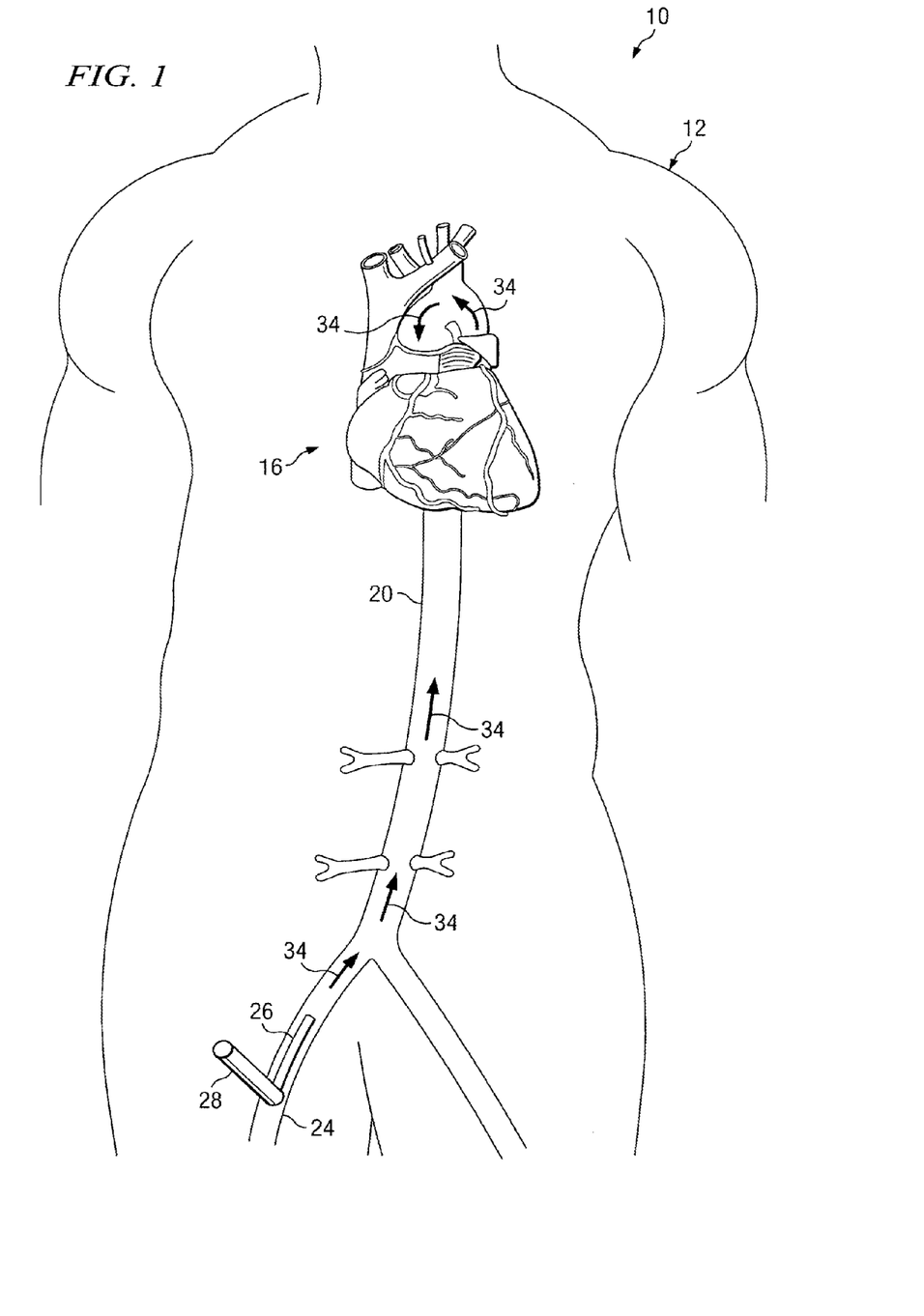
FIG. 1 is a simplified schematic diagram illustrating a patient that may subjected to an example cardiovascular procedure.

Referring back to FIG. 1, FIG. 1 offers a sponge system 10 that is designed to overcome these shortcomings, and others, in offering an optimal solution for embolic protection. FIG. 1 includes a patient 12, having a heart, which is generally indicated at 16, and an aorta 20 that extends from heart 16, along the spinal cord, and to the legs of patient 12. For purposes of performing a cardiovascular procedure, a surgeon may create an entry point 24, from which a catheter 26 may be inserted. A simple gripping mechanism or an introductory element 28 (e.g. a plastic tube) may be provided to adjust or to manipulate catheter 26 to any suitable location. Introductory element 28 is generally just part of the introductory sheath system, which can accommodate particular curvatures and remain at entry point 24 of patient 12 throughout the procedure. In certain embodiments, introductory element 28 can be used for flushing operations and, further, be used to ensure that air or clots are not present during the procedure. The introductory sheath generally includes a lumen that is sufficient to accommodate all of the equipment identified herein (e.g. balloon, stent, sponge, etc.). In the coronary system (or in rentals, in carotids, in vein grafts, etc.), the lumen could be in the range of 1.0-8.0 millimeters in diameter and/or be designed based on particular needs. (Note that most vein grafts may generally be in the range of 3.0-6.0 millimeters. In aorta systems, this range could be much higher (e.g. 30-60 millimeters in diameter)).

Catheter 26 may be fed through entry point 24 and propagate along aorta 20 until it reaches its intended destination. A series of arrows 34 are provided in order to illustrate one example pathway associated with sponge system 10, whereby the attending surgeon may guide catheter 26 in any suitable fashion. In operation of an example embodiment, a sheath may be placed in the right or left groin, whereby entry point 24 is incised at the femoral artery. The sheath would be positioned at entry point 24. The sheath is simply a tube of some type (e.g. plastic, glass, etc.) that can be used as a conduit and from which other instruments may be delivered.

Catheter 26 could then be placed in entry point 24 and propagate along aorta 20. Sponge system 10 could be inserted at entry point 24, as the sheath can easily constrain any sponge arrangement. Sponge system 10 would then offer embolic protection at the target site, which may be determined by the treating physician. Sponge system 10 can filter particles, while allowing blood to pass through a given region. Additional details relating to this process and the capabilities of sponge system 10 are provided below with reference to FIGS. 2-6.

Figure 2:
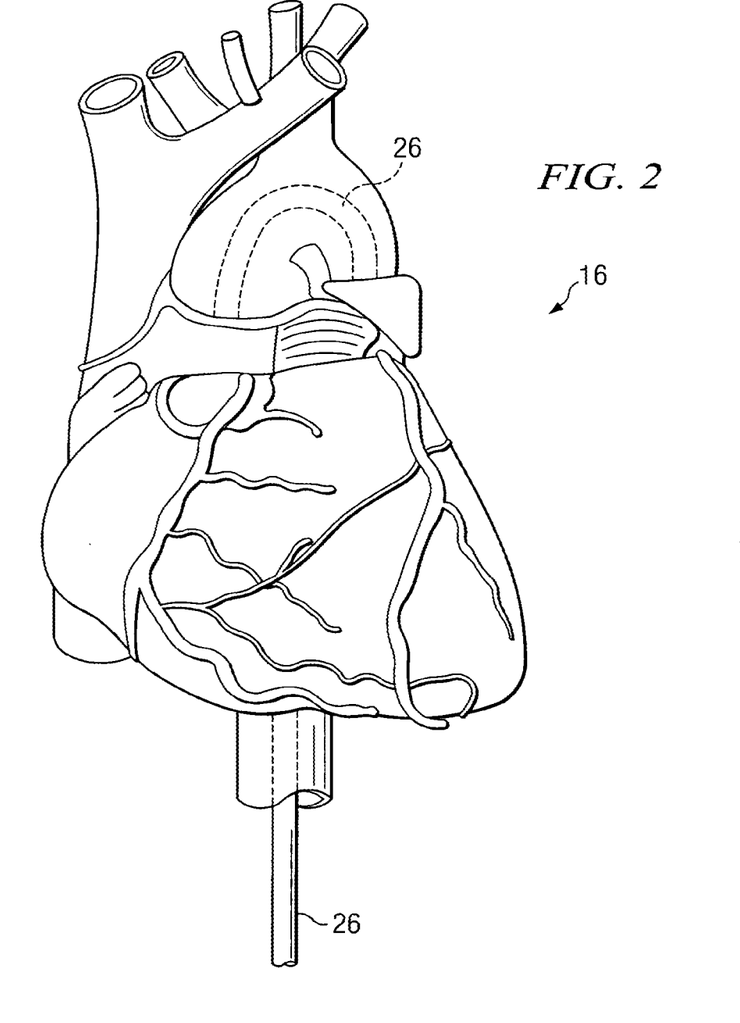
FIG. 2 is a simplified schematic of a heart within the patient of FIG. 1.

Referring now to FIG. 2, FIG. 2 illustrates additional details associated with the procedure described above. FIG. 2 is a simplified schematic diagram of heart 16 of FIG. 1. For purposes of example and teaching, heart 16 is described as experiencing a number of blockages such that a balloon procedure is recommended for patient 12. In particular, patient 12 had a previous blockage (some ten years ago) that necessitated a bypass operation of a coronary artery. Now, patient 12 is experiencing chest pain, dizziness, etc. because of a narrowing in a given vein (presumably from his leg) associated with this bypass. The balloon procedure that was elected could readily employ sponge system 10 to prevent debris from traveling to undesired locations. Note that such debris is detrimental and lethal to patient 12, as it can easily cause heart attacks, strokes, and/or form future blockages for patient 12. In other scenarios, such debris could lead to kidney failures, amputations, etc.

In a normal balloon procedure, which could ostensibly include a stent or any other appropriate device, while patient 12 is awake, catheter 26 is inserted into an artery at the top of the leg (i.e. the femoral artery) at entry point 24. The procedure generally begins with the doctor injecting some local anesthesia into the groin area and putting a needle into the femoral artery (the blood vessel that runs from the heart down the leg). Once the needle is inserted, a guide wire is placed through the needle and into the blood vessel. Following this step, the guide wire is left in the blood vessel and the needle is removed.

A flexible system, often called an "introducer," is placed over the guide wire and the guide wire is removed. Next, a diagnostic catheter, which is a long narrow tube, is advanced through the introducer over a guide wire and into the blood vessel. The catheter is then guided to the aorta and the guide wire is removed. Once the catheter is placed in the opening of one of the coronary arteries, the doctor may inject dye and/or take a series of images.

Figure 3:
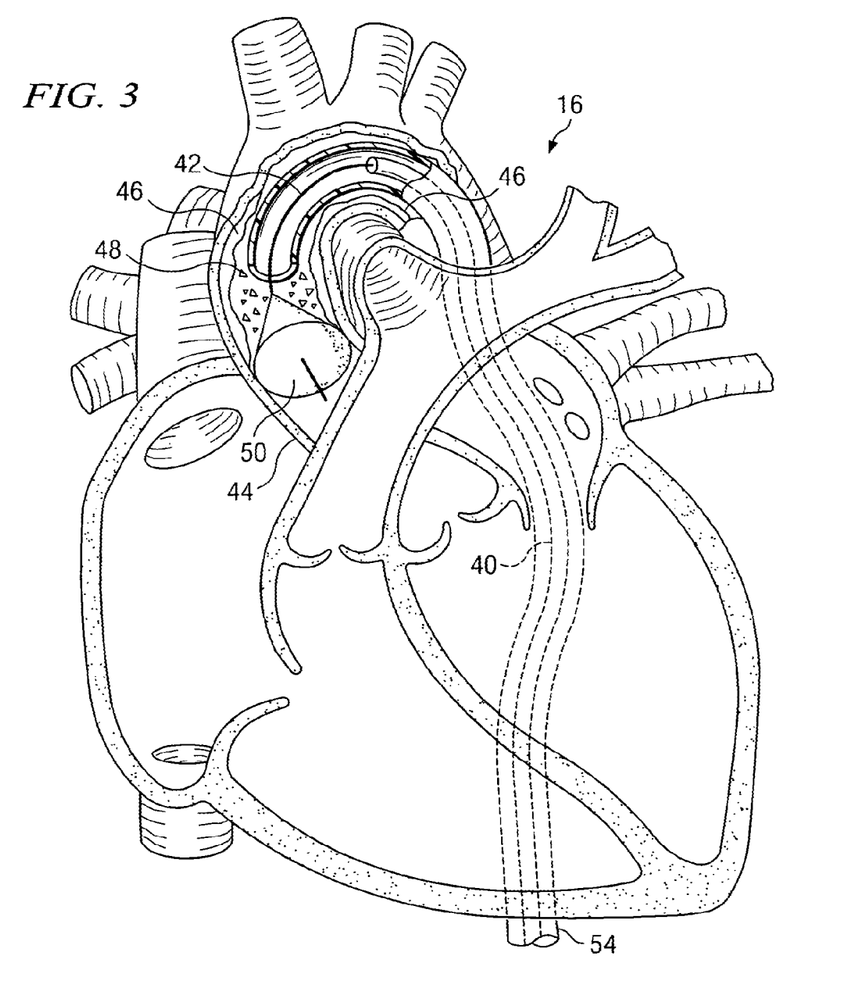
FIG. 3 is a simplified schematic diagram of a sponge system that may be used in the heart of FIG. 2.

FIG. 3 illustrates additional details related to the balloon procedure. FIG. 3 is a simplified schematic diagram of heart 16, which includes a bypass 44 (i.e. a leg vein) that is experiencing a current blockage. Bypass 44 includes various formations of plaque 46, which may flake off and produce debris 48. FIG. 3 also illustrates a guide 40, which is accompanied by a guide wire 42 and a sheath 54. Note that a portion of sheath 54 and guide 40 is behind heart 16, which is why they are illustrated by dashed lines at certain locations. Through guide 40, sheath 54 and all other requisite materials are passed (e.g. introductory catheter, delivery catheter, removal catheter, sponge configuration, etc.). A sponge 50 is also provided that is suitably fixed to guide wire 42. Note that guide wire 42 may be of any suitable length: such length being determined based on particular needs or specific environments. For example, shorter guide wires 42 may be used in carotid procedures.

Continuing with the balloon procedure, the first catheter is exchanged-out over guide wire 42 for a guiding catheter. Potentially, a smaller guide wire is also advanced across the blocked section of the vein and a balloon-tipped tube is generally positioned so the balloon part of the tube is beside the blockage. The balloon is then inflated for a few seconds to compress the blockage against the wall of the vein. Then the balloon is deflated.

The doctor may repeat this inflation technique a few times, each time pumping up the balloon a little more to widen the passage for the blood to flow through the conduit. This treatment is routinely repeated at each blocked site in the coronary arteries. A stent (not shown) may then be placed at the now-unblocked passageway. A stent is a latticed, metal scaffold that is placed within the coronary artery (or vein in this example) to keep the vessel open.

During all of these procedures, debris 48 is likely to be present. The debris is detrimental to patient 12 and, thus, needs to be accounted for. In the example of FIG. 3, a triangular, cone-shaped sponge 50 is suitably positioned to capture any debris 48 that is prevalent during the procedure.

Debris 48 from plaque (or any other source) can generally flake off and propagate downstream. Debris is generally friable and normally involves multiple layers. For example, a hard layer of plaque may be present in a given vessel, whereby softer material is present at a surface level. Surface material is particularly detrimental, as it is easily distributed by instruments (which are often metal) used in most cardiovascular procedures. Free moving (uncaptured) debris 48 can naturally cluster and subsequently clog or block a vessel, which could produce a heart attack. The same scenario can involve a carotid artery. For example, during a routine stent or balloon procedure, debris 48 can be present and, thereby, cause any of the aforementioned problems: particularly stroke. Hence, in other applications, sponge 50 could address this vulnerability and, thus, be rather large (e.g. 30-60 millimeters). This sponge arrangement could cover an entire aorta. This could involve protection in neck arteries. However, larger sponges would require greater expertise and dexterity on the part of the operating surgeon, as larger sponges are more difficult to remove/withdraw.

Sponge 50 may be suitably coupled to guide wire 42 in any appropriate manner. This may include a piercing of sponge 50, whereby some type of stop mechanism is provided at the end of sponge 50. Alternatively, sponge 50 may be glued to guide wire 42 or slide freely along guide wire 42, where appropriate. In other scenarios, sponge 50 may be molded around guide wire 42. The present invention contemplates considerable flexibility in the manner in which sponge 50 is fixed: either to guide wire 42 or to any other suitable element in order to facilitate its operations.

While the surgeon or the technician is performing any number of tasks associated with patient end user 12, debris 48 is effectively captured by sponge 50. Concurrently, blood flow continues, as sponge 50 does not unnecessarily restrict the downstream propagation of blood. Hence, sponge 50 is continuously providing protection for patient 12, while optimizing blood flow during the operation. No longer would a device necessarily occlude an entire portion of the heart (although in certain applications, sponge 50 can completely restrict blood flow). Nor would such a device traumatize a given area, which may be subjected to jostling and shifting caused by the procedure.

Hence, sponge system 10 is adequately configured such that it facilitates blood flow as it protects against harmful debris 48. Hence, a perfusion-type mechanism is achieved concurrently with capturing destructive debris that have a propensity to flow downstream of the surgical (or intervened) area. In certain instances (e.g. in certain procedures involving the aorta), no blood flow is desired to propagate downstream. Sponge 50 could readily accommodate these scenarios and completely restrict blood flow in these instances.

Note also that the intrinsic nature of sponges allows them to be retracted quite easily. Because of their compression properties, as well as their malleability, sponges are ideal in such cardiovascular procedures. Each sponge 50 may be designed with any appropriate porosity properties such that only the proscribed amount of perfusion is achieved. Similarly, sponge 50 may be designed only to swell to a certain degree or to hold only a specific amount of debris or fluid at any one time. Note that sponge 50 may be designed such that optimal control of blood flow is achieved. For example, in a sponge system that includes a circular design (having a number of spherical shapes for example), a number of holes could be provided in the elements so that the blood flow could go through a single unit and then flow to the next unit. In this fashion, a number of holes could accommodate perfusion, but also be able to redirect blood flow from one unit to the next. Hence, holes could readily be provided in any given sponge 50: some of the holes being offset from each other in certain instances. Any such configurations or any permutations of these concepts are clearly within the scope of the present invention.

In other instances, sponge 50 may be designed to completely occlude a given area. In addition, each sponge 50 may be constructed with a specific rigidness or flexibility (e.g. on a scale from 'soft' to 'hard'). Thus, sponge 50 may include properties that may be based on particular needs and configurations. Note that blood is about 8 microns. The material to be caught by sponge 50 can be in the range of 15-200 microns. In alternative embodiments, sponge 50 may be designed with any requisite properties where appropriate and be specific to individual applications.

Thus, sponge 50 offers an architecture that can easily conform to the shape of the target location. This would allow the present invention to have a broad range of applications. Moreover, sponge 50 is atraumatic, as it offers only a minimal disruption to an associated region. Therefore, during a normal stent or balloon procedure, debris 48 would remain relatively undisturbed during the operation. In the unlikely chance that debris 48 would materialize or surface, then sponge 50 would be prepared to capture it.

Hence, the sponge configuration is "always on," providing a solution that is continuously deployed and that consistently protects any vulnerable area within a given patient. Sponge 50 is always actuated, which provides a number of additional ancillary benefits. For example, because of the "always on" characteristic, a physician is no longer burdened with having to trigger any type of filtering mechanism while he is performing a procedure. Also, sponge 50 is completely actuated once it emerges from a delivery catheter or guide 40. This actuation exists during a procedure, during preparation for the procedure, and during the post-procedure tasks (e.g. extracting instruments). Sponge 50 only ceases being effective once it has been removed from the patient site. As identified above, sponge 50 also provides for enhanced versatility in its applications, as it can readily be applied to virtually any procedure.

Figure 4A:
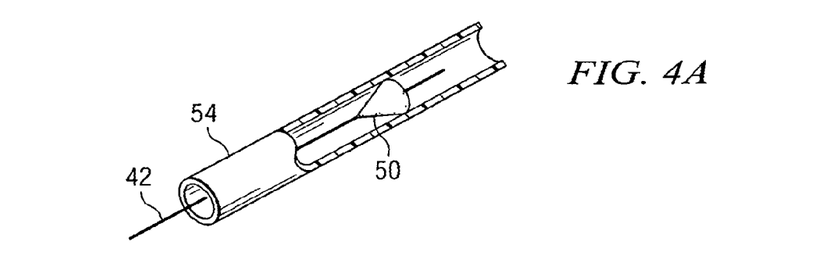
FIGS. 4A, 4B, and 4C are simplified schematic diagrams of the sponge system: collectively demonstrating one potential deployment and extraction thereof.
Figure 4B:
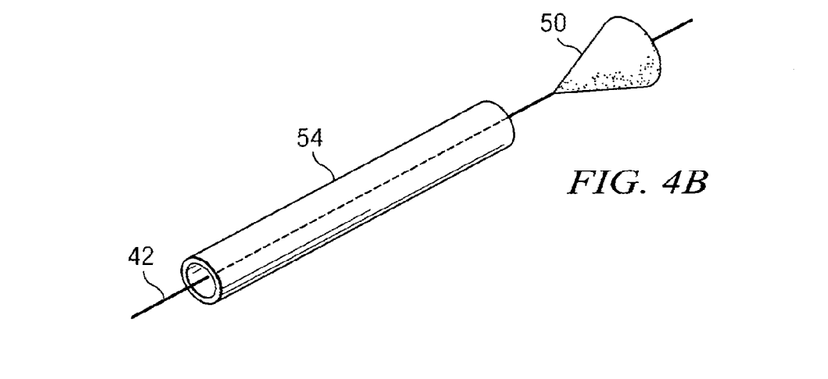
Figure 4C:
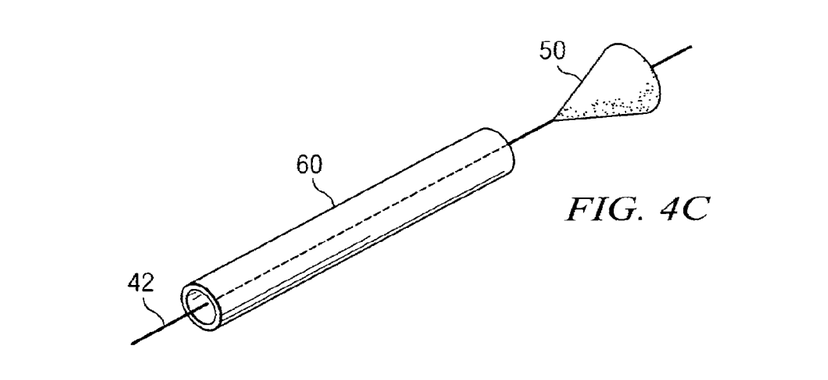

FIGS. 4A, 4B, and 4C are simplified schematic diagrams of sponge 50 and one potential deployment/extraction thereof. In operation, the sponge (or sponges) can be loaded into sheath 54 and/or guide 40 in order to initiate the embolic protection mechanism of the present invention. Sponge 50 may be suitably compressed within sheath 54 before being inserted into patient 12. Once the associated cardiovascular procedure has been completed, sponge 50 may then be properly withdrawn with minimal effort and little trauma to patient 12. Sponge 50 could readily be collapsed into (constraining) sheath 54 such that is can extend beyond the target area. Once constraining sheath 54 has released sponge 50, sponge 50 is ready to begin capturing the debris.

In retrieving sponge 50, an extraction sheath 60 may be utilized. This is illustrated in FIG. 4C. In one embodiment, extraction sheath 60 may be slightly larger than sheath 54. Additionally, extraction sheath 60 may be used for aspiration (e.g. removing fluids or gases with a suction device). Extraction sheath 60 would also allow some of the debris collected by sponge 50 to be removed before the surgical cite is exited.

Sponge 50 may be designed to have enough filtering capability to adequately collect materials at a surgical area. Unlike other filtration systems, sponge 50 may be designed in a particular embodiment to include porosity characteristics that allow for blood flow for areas downstream of the target area.

The human body can generally tolerate approximately 2-3 minutes of a lack of blood flow in most cardiovascular procedures. However, balloon and stent procedures can easily take 5-6 minutes, and even extend further in some instances. Moreover, such procedures generally implicate a number of individuals, who have to participate in the procedure. The architecture of sponge 50 does not starve the downstream area of blood flow needlessly (unless such a deprivation is preferred, in which case sponge 50 can accommodate this). This, in turn, effectively removes the limited timing constraints, which are present in other systems. In addition, such a system can be operated by a single physician, which avoids complexity and unnecessary coordination amongst an entire team of cardiologists (or physicians). Also, this elimination of participants and complexity is amendable to condensed surgical procedures. A significant number of precautions and steps are effectively avoided as a result of the configuration of sponge system 10.

Figure 5A:
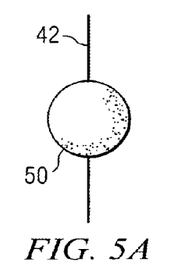
Figure 5B:
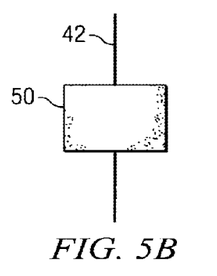
Figure 5C:
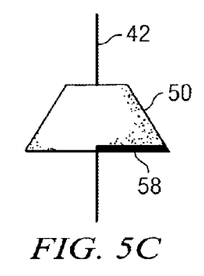
Figure 5D:
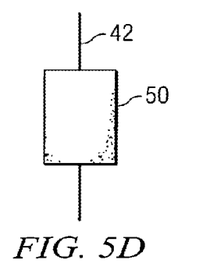
Figure 5E:
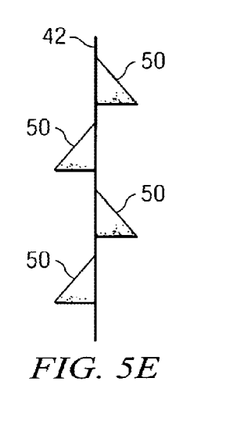
Figure 5F:
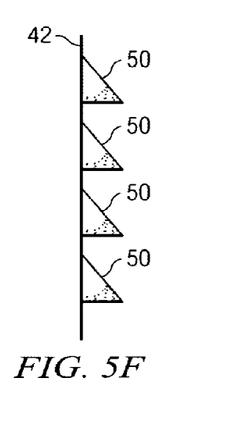
Figure 5G:
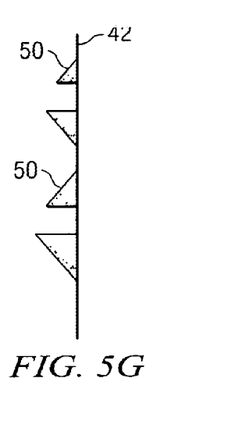
Figure 5H:
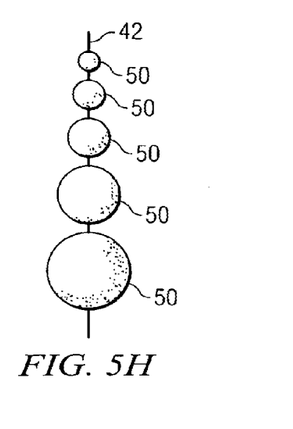
Figure 5I:
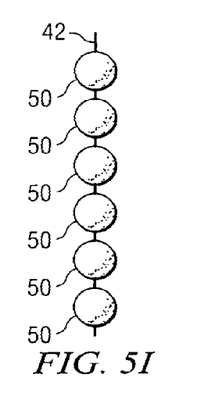
Figure 5J:
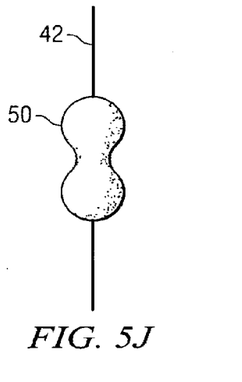

FIGS. 5A-N are simplified schematic diagrams of various example configurations of sponge system 10 according to some of the teachings of the present invention. FIG. 5A is a circular-shaped sponge 50; FIG. 5B is a square-shaped sponge 50; FIG. 5C is a trapezoid-shaped sponge 50; FIG. 5D is a rectangular-shaped sponge 50; FIG. 5E is a triangular-shaped configuration sponge 50 arrangement, which includes an alternating pattern; FIG. 5F is a triangular-shaped series configuration sponge 50 arrangement; FIG. 5G is a triangular-shaped configuration sponge 50, which uses opposing elements; FIG. 5H is a circular-shaped sponge 50 arrangement that includes progressively larger elements; FIG. 5I is a circular-shaped sponge 50 configuration that includes a series of elements; and FIG. 5J is an hourglass-shaped sponge 50. Note that the examples of FIG. 5 offer just some of the possible arrangements of a given sponge in accordance with the teachings of the present invention. These designs may be changed, modified, combined, or added to where appropriate and based on particular needs. Using analogous reasoning, it should be noted that these arrangements are not exhaustive, as other alternatives and permutations of sponge 50 are clearly within the broad scope of the present invention.

Note that the series configurations (i.e. multiple sponge elements being provided along a given wire or guide) illustrated in FIG. 5 are conducive to utilization in smaller catheters, as well as reductions in other ancillary equipment. Thus, a series of sponges 50 can effectively be used to gather and collect all debris 48 in confined target areas.

Note that a series of edges 58 (e.g. on every edge or at any selected and appropriate location of sponge 50) could also be provided on any of sponges 50. Edges 58, which are illustrated in FIG. 5C, could be used to avoid snagging (and/or trauma), as sponge 50 is removed. Edges 58, which may be plastic or constructed of any other suitable snag-resistant material, may be provided in any of the other embodiments as described herein. In addition, a somewhat elastic coating (e.g. plastic) could be placed on the entire surface of sponge 50 such that the aforementioned snagging issue is effectively avoided. The coating could provide an overall resiliency to sponge 50.

In still other embodiments, drug delivery could be facilitated by the present invention, whereby sponge 50 is coated with some agent (e.g. for stimulating growth or rapid healing, for alleviating pain or discomfort, for thinning blood, etc.). Once suitably positioned, the drug could release at the surgical site or via the blood stream of patient 12.

Figure 5K:
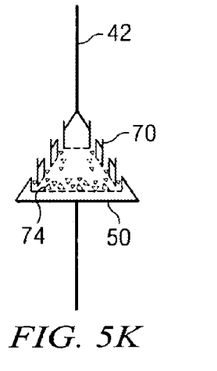
Figure 5L:
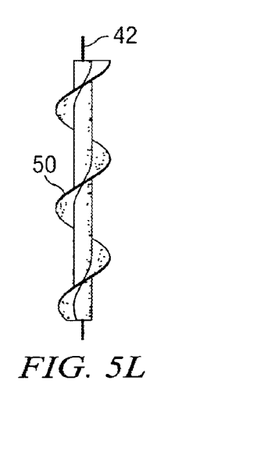
Figure 5M:
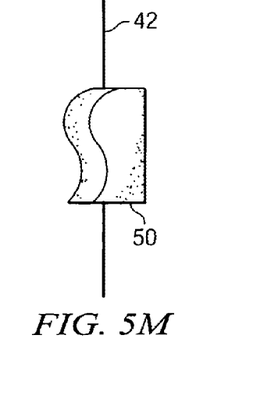
Figure 5N:
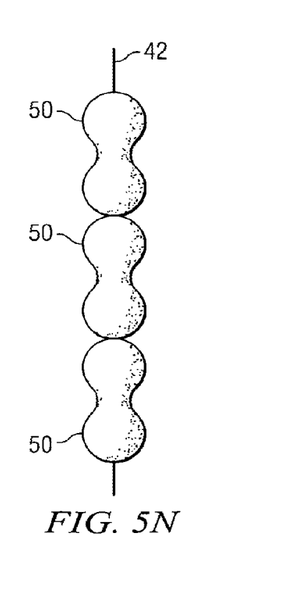

FIG. 5K illustrates a series of grooves 70, which can be used to collect or to direct blood flow to a reservoir 74. Note that as used herein in this document, "grooves" refers to any slat, hole, pore, crease, or opening that affects or influences the direction of blood flow or plaque. Note also that grooves 70 have been exaggerated in the illustration to emphasize their ability to direct blood flow or plaque. In other embodiments (e.g. those that involve simple holes and/or pores), grooves 70 could be relatively small and formed into any particular shape (e.g. circle, square, slat, triangle, etc.). Unlike conventional sponges that universally collect matter on their surfaces, sponge 50 may be designed in order to have the collected contents deposited internally (i.e. in reservoir 74). Hence, sponge 50 allows preferential areas within its internal structure to receive the collected debris. Thus, the collected material (debris 48) is internalized: as opposed to externalized, which can be problematic when removing sponge 50. Loose debris 48 could be an issue during removal of any of the equipment identified herein. Hence, any sponge 50 could use the groove-reservoir arrangement. Corkscrew and whirlwind configurations could also be used to capture debris 48 in accordance with the present invention. These are illustrated in FIGS. 5L-M. Lastly, FIG. 5N illustrates a series of connected circular sponges 50, which have no space between them. This offers yet another example configuration of sponge 50.

Note that, as identified above, sponge 50 may be designed in a way such that optimal perfusion occurs. For example, in the context of FIG. 5N, a series of pores or holes could be provided in each lobe. One lobe could have more pores than another lobe. Using these pores or holes (which are included within the broad rubric of grooves), perfusion can be controlled. The placement and/or size of the holes could similarly be manipulated to achieve the effect that is desired.

Figure 6:
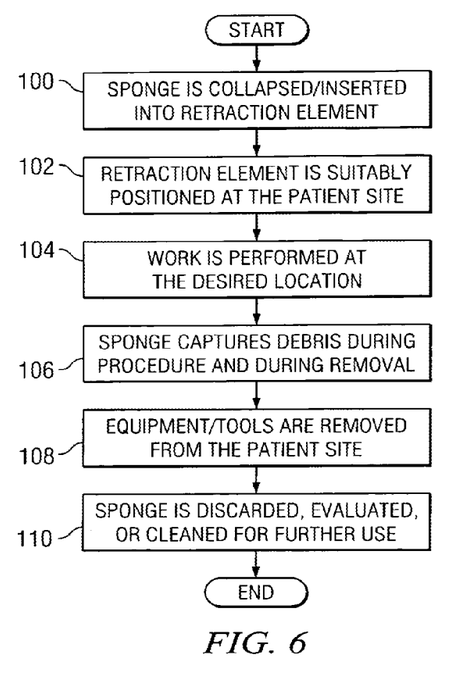
FIG. 6 is a simplified flowchart illustrating a number of general steps associated with one implementation of the sponge system.

FIG. 6 is a simplified flowchart illustrating a series of example steps associated with sponge system 10. The method may begin at step 100 where sponge 50 is collapsed and inserted into a given retraction element (e.g. a guide, a catheter, a sheath, etc.). At step 102, the retraction element is suitably positioned at the surgical area. Work is then performed at the surgical area (e.g. an angioplasty, a stent procedure, a bypass, a balloon procedure, etc.). At step 106, sponge 50 effectively captures any debris (or other materials) that are present and which are unwanted. The capturing capability is activated the moment that sponge 50 emerges from the retraction element.

Equipment and tools are then removed from the patient site at step 108. While being removed, sponge 50 potentially performs a sweeping and/or a cleaning function. Sponge 50 may then be discarded, evaluated (e.g. for biopsy studies), or cleaned for future use where appropriate. In the case of a biopsy, all of the material collected by sponge 50 (not just debris) may be evaluated.

It is important to note that the stages and steps in FIG. 6 illustrate only some of the possible scenarios that may be executed by, or within, the present system. Some of these stages and/or steps may be deleted or removed where appropriate, or these stages and/or steps may be modified or changed considerably without departing from the scope of the present invention. In addition, a number of these operations have been described as being executed concurrently with, or in parallel to, one or more additional operations. However, the timing of these operations may be altered considerably. The preceding example flows have been offered for purposes of teaching and discussion. Substantial flexibility is provided by the tendered architecture in that any suitable arrangements, chronologies, configurations, and timing mechanisms may be provided without departing from the broad scope of the present invention.

Note also that the example embodiments described above can be replaced with a number of potential alternatives where appropriate. The processes and configurations discussed herein only offer some of the numerous potential applications of sponge system 10. The elements and operations listed in FIGS. 1-6 may be achieved with use of sponge system 10 in any number of contexts and applications. Accordingly, suitable infrastructure may be included within sponge system 10 to effectuate the tasks and operations of the elements and activities associated with managing embolic protection.

Although the present invention has been described in detail with reference to particular embodiments in FIGS. 1-6, it should be understood that various other changes, substitutions, and alterations may be made hereto without departing from the sphere and scope of the present invention. For example, although the preceding FIGURES have referenced a number of components as participating in the numerous outlined procedures, any suitable equipment or relevant tools may be readily substituted for such elements and, similarly, benefit from the teachings of the present invention. These may be identified on a case-by-case basis, whereby a certain patient may present a health risk factor while another (with the same condition) may not. Hence, sponge 50 may be designed based on particular needs with particular scenarios envisioned. This could include modifying (cutting, trimming, compressing, combining with any other element, etc.) sponge 50 by the surgeon 'in situ' or prior to the surgery.

In other alternatives, a retraction (or export or extraction) catheter may not even be necessary. In such a scenario, sponge 50 could perform a final sweeping or cleaning function for the target area, as highlighted supra. Because of the inherent properties of sponge 50, it is generally resistant to snagging and, thus, could easily perform such an operation with little trouble.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims. In order to assist the United States Patent and Trademark Office (USPTO) and additionally any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of filing hereof unless the words "means for" are specifically used in the particular claims; and (b) does not intend by any statement in the specification to limit his invention in any way that is not otherwise reflected in the appended claims.

What is claimed is:

1. A method, comprising:
   positioning a sponge system in an area of a patient who is to undergo a cardiovascular procedure, wherein the sponge system includes a series of two or more sponges, wherein each of the two or more sponges includes at least one groove configured to enable a portion of blood flow to pass through the grooves,
   wherein the sponge system is operable to collect debris present in or proximate to the area and to allow a portion of the blood flow to pass through the sponge concurrently, and
   wherein the at least one groove of one of the two or more sponges is offset from the at least one groove of an adjacent one of the two or more sponges.

2. The method of claim 1, wherein the sponge system is coupled to a guide wire.

3. The method of claim 2, wherein the sponge system includes a stop mechanism to fix the sponge system at a position on the guide wire.

4. The method of claim 2, wherein the sponge system is slidably coupled to the guide wire.

5. A method, comprising:
- positioning a sponge system in an area of a patient who is to undergo a cardiovascular procedure,
- wherein the sponge system is operable to collect debris present in or proximate to the area,
- wherein the sponge system is configured with one or more grooves to allow a portion of blood flow associated with the area to pass through the one or more grooves while the debris is collected,
- wherein a distal end of a sponge of the sponge system includes an edge configured with a snag-resistant material, wherein a remaining portion of the sponge is not configured with the snag-resistant material, and wherein the sponge is tapered from a smaller diameter at a proximal end to a larger diameter at the distal end.

6. The method of claim 5, wherein the sponge system is coupled to a guide wire.

7. The method of claim 6, wherein the sponge system is slidably coupled to the guide wire.

8. The method of claim 6, wherein the sponge system includes two or more sponges.

9. The method of claim 8, wherein each of the two or more sponges includes a groove configured to enable the blood flow to pass through the groove.

10. The method of claim 9, wherein the groove of one of the sponges is offset from the groove in an adjacent one of the sponges.

11. The method of claim 5, wherein a coating is disposed on at least a portion of the sponge system, the coating operable to limit friction or snagging.

* * * * *